United States Patent
Matsumoto

(10) Patent No.: US 10,495,521 B2
(45) Date of Patent: Dec. 3, 2019

(54) SENSOR SUBSTRATE AND SENSOR APPARATUS

(71) Applicant: KYOCERA Corporation, Kyoto-shi, Kyoto (JP)

(72) Inventor: Hiroshi Matsumoto, Kyoto (JP)

(73) Assignee: KYOCERA Corporation, Kyoto-shi, Kyoto (JP)

( * ) Notice: Subject to any disclaimer, the term of this patent is extended or adjusted under 35 U.S.C. 154(b) by 0 days.

(21) Appl. No.: 16/095,044

(22) PCT Filed: Apr. 26, 2017

(86) PCT No.: PCT/JP2017/016582
§ 371 (c)(1),
(2) Date: Oct. 19, 2018

(87) PCT Pub. No.: WO2017/188326
PCT Pub. Date: Nov. 2, 2017

(65) Prior Publication Data
US 2019/0101457 A1 Apr. 4, 2019

(30) Foreign Application Priority Data
Apr. 26, 2016 (JP) .................. 2016-088162

(51) Int. Cl.
*G01K 7/18* (2006.01)
*G01K 7/02* (2006.01)
*G01N 27/403* (2006.01)

(52) U.S. Cl.
CPC .............. *G01K 7/18* (2013.01); *G01K 7/021* (2013.01); *G01N 27/403* (2013.01)

(58) Field of Classification Search
CPC .......... H01C 7/18; H01C 7/021; H01C 1/032; H01C 1/028; G01K 7/18; G01K 7/021
See application file for complete search history.

(56) References Cited

U.S. PATENT DOCUMENTS

| | | | | |
|---|---|---|---|---|
| 5,242,225 A * | 9/1993 | Kasanami | ............. | H01C 7/021 338/25 |
| 6,653,926 B1 * | 11/2003 | Zitzmann | ................ | G01K 7/18 338/25 |
| 7,746,212 B2 * | 6/2010 | Zitzmann | ............... | G01K 7/186 338/22 R |
| 8,333,506 B2 * | 12/2012 | Kamenov | ............. | G01K 7/183 338/22 R |
| 10,247,620 B2 * | 4/2019 | Matsumoto | ............. | G01K 7/18 |
| 2004/0056321 A1 * | 3/2004 | Parsons | .................. | G01F 1/692 257/417 |
| 2009/0173526 A1 * | 7/2009 | Kloiber | .................... | G01K 1/14 174/260 |

FOREIGN PATENT DOCUMENTS

| JP | 02-171626 A | 7/1990 |
|---|---|---|
| JP | 11-121214 A | 4/1999 |
| WO | 2015/163278 A1 | 10/2015 |

* cited by examiner

*Primary Examiner* — Kyung S Lee
(74) *Attorney, Agent, or Firm* — Volpe and Koenig, P.C.

(57) ABSTRACT

A sensor substrate includes an insulating substrate, an electrode disposed on a principal face of the insulating substrate, a resistor wiring section in a form of multiple layers located within the insulating substrate, the multiple layers being disposed in a thickness direction of the insulating substrate, and a widened metallic layer disposed so as to overlap the electrode, as seen in a transparent plan view of the sensor substrate.

19 Claims, 7 Drawing Sheets

SENSOR SUBSTRATE AND SENSOR APPARATUS

TECHNICAL FIELD

The present invention relates to a sensor substrate including an insulating substrate formed of a ceramic sintered body and a resistor wiring section disposed in the insulating substrate, and to a sensor apparatus.

BACKGROUND ART

There is a heretofore known sensor substrate, which is used for an exhaust gas sensor, etc., that achieves temperature detection by utilizing the variation of electrical resistance in a metal material with temperature. For example, use has been made of a sensor substrate comprising an insulating substrate formed of a ceramic sintered body such as an aluminum oxide sintered body, and a resistor wiring disposed on the insulating substrate and including an electrode (refer to Japanese Unexamined Patent Publication JP-A 11-121214 (1999)).

SUMMARY OF INVENTION

Technical Problem

However, the above-described sensor substrate may pose the following imperfections. That is, for example, in detecting combustion exhaust gas of various types, due to migration (diffusion) of metal ions such as calcium ions contained in glass constituting the insulating substrate toward the electrode (cathode) of the sensor substrate, a void, etc. is developed in the insulating substrate, causing deformation of the resistor wiring, and, the consequent formation of a narrow part, viz., a part with a reduced cross-sectional area, of the resistor wiring may lead to an increase in resistance in the resistor wiring.

Solution to Problem

According to one aspect of the invention, a sensor substrate comprises: an insulating substrate; an electrode disposed on a principal face of the insulating substrate; a resistor wiring section in a form of multiple layers located within the insulating substrate, the multiple layers being disposed in a thickness direction of the insulating substrate; and a widened metallic layer disposed so as to overlap the electrode as seen in a transparent plan view of the sensor substrate.

According to another aspect of the invention, a sensor apparatus comprises: the sensor substrate mentioned above; and an external substrate connected with the sensor substrate.

Advantageous Effects of Invention

The sensor substrate according to one aspect of the invention comprises: the insulating substrate; the electrode disposed on the principal face of the insulating substrate; the resistor wiring section in the form of multiple layers located within the insulating substrate, the multiple layers being disposed in the thickness direction of the insulating substrate; and the widened metallic layer disposed so as to overlap the electrode as seen in the transparent plan view of the sensor substrate. In this construction, for example, in detecting combustion exhaust gas of various types, even if metal ions such as calcium ions contained in glass constituting the insulating substrate are caused to migrate (diffuse) toward the electrode (cathode) of the sensor substrate, the widened metallic layer, which overlaps the electrode as seen in the transparent plan view, restrains the metal ions against migration toward the electrode. This makes it possible to protect the insulating substrate from development of voids, etc., and render the resistor wiring section less deformable for a reduction in the formation of a part subjected to a change in cross-sectional area, and thereby reduce the variation of resistance in the resistor wiring section.

The sensor apparatus according to another aspect of the invention comprises the sensor substrate mentioned above, and therefore the detection accuracy of temperature variation can be increased.

DESCRIPTION OF EMBODIMENTS

A sensor substrate in accordance with an embodiment of the invention will be described with reference to accompanying drawings. Note that the top and bottom of the construction to be referred to are specified just for convenience in explanation, and this arrangement is not intended to be limiting of the orientation of the sensor substrate, etc. in actual use.

Figure 1:
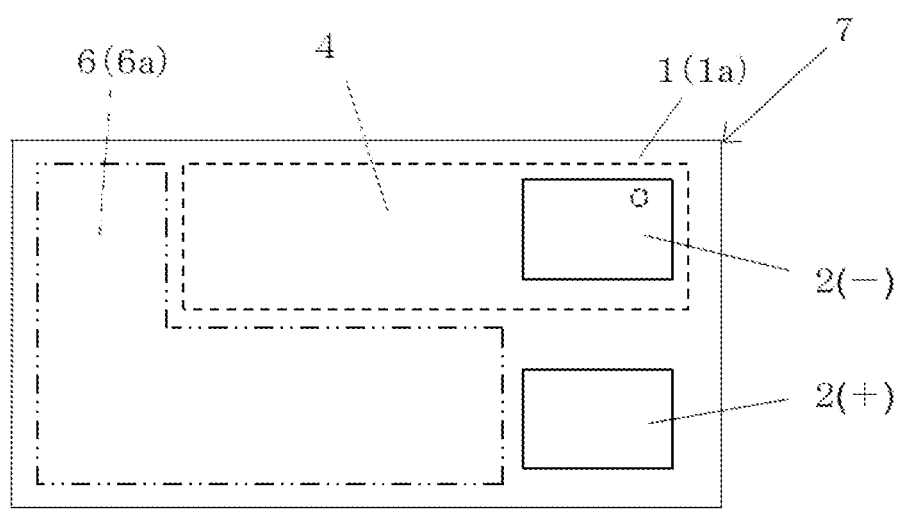
FIG. 1 is a transparent plan view showing a sensor substrate of the invention.

As shown in FIGS. 1 to 7, a sensor substrate 7 comprises: an insulating substrate 1 in which a plurality of insulating layers 1a are laminated; an electrode 2 disposed on a principal face of the insulating substrate 1; a resistor wiring section 3 in the form of multiple layers located within the insulating substrate 1, the multiple layers being disposed in a thickness direction of the insulating substrate 1; and a widened metallic layer 4 disposed so as to overlap the electrode 2 as seen in a transparent plan view. FIG. 1 represents a top view of the sensor substrate 7, illustrating an upper insulating layer 1a in a see-through manner to identify the metallic layer 4. Temperature measurement is carried out utilizing the fact that electrical resistance in the resistor wiring section 3 varies according to temperature. That is, for example, the temperature of an environment where the sensor substrate 7 is located is calculated and detected on the basis of the measured value of the electrical resistance of the resistor wiring section 3. The electrode 2 may be formed not only on the top surface of the insulating substrate 2 but also on the bottom surface thereof.

The insulating substrate 2, which is shaped, for example, in a quadrangular flat plate, serves as a base portion provided with the resistor wiring section 3 in electrically insulated condition. The insulating substrate 2 is formed of a ceramic sintered body such for example as an aluminum oxide sintered body, an aluminum nitride sintered body, a mullite sintered body, a glass ceramic sintered body, or zirconia ceramics (a zirconium oxide sintered body). The insulating substrate 2 is composed of a stack of a plurality of insulating layers 1a (five insulating layers 1a in the case shown in FIG. 2) formed of such a ceramic sintered body.

For example, where the insulating layers 1a are each formed of an aluminum oxide sintered body, the insulating substrate 2 may be produced in the following manner. As the first step, powder of raw materials such as silicon oxide ($SiO_2$), magnesium oxide (MgO), and manganese oxide ($Mn_2O_3$) serving as sintering aids is added to powder of aluminum oxide ($Al_2O_3$), and, after further addition of suitable binder, solvent, and plasticizer, the admixture is kneaded into a slurry. After that, the slurry is made in a sheet-like form by a heretofore known technique such as the doctor blade method or the calender roll method to obtain a ceramic green sheet. The ceramic green sheet is subjected to suitable punching operation, and, on an as needed basis, a plurality of ceramic green sheets are stacked one upon another, followed by a high-temperature (about 1300 to 1600° C.) firing process. Each of the plurality of ceramic green sheets becomes the insulating layer 1a. The insulating substrate 1 comprises glass 2c containing calcium (Ca), magnesium (Mg), etc.

The resistor wiring section 3 is formed of platinum, which is a metal material whose electrical resistance varies according to temperature, or a metal material predominantly composed of platinum. It is preferable that an absolute value of the electrical resistance of the resistor wiring section at a reference temperature ((for example, so-called room temperature such as about 25° C.) is large in order to detect the variation in electrical resistance of the metal material according to temperature.

This is due to the following reason. That is, the variation of electrical resistance in the resistor wiring section 3 according to temperature occurs at a constant rate irrespective of the magnitude (absolute value) of electrical resistance at the reference temperature. Namely, the larger the value of electrical resistance at the reference temperature, the larger the absolute value of the variation of electrical resistance according to temperature becomes. The larger an absolute value of the electrical resistance variation is, the less susceptible to noise (electrical resistance variation caused by other factor than a change in temperature) it is. In addition, measurement is also made easier. Accordingly, it is preferable that the resistor wiring section 3 exhibits greater electrical resistance at the reference temperature. Thus, the metal material in use, e.g. platinum is given a linear form (namely, a form effective in providing a long electrical resistance measurement zone and increasing the absolute value of electrical resistance).

In the metal material predominantly composed of platinum, the constituents (type) and content of other element than platinum are suitably selected to achieve adjustment of the temperature coefficient of resistance (TCR) of the resistor wiring section 3, and to achieve improvement in heat resistance. Examples of the element other than platinum include platinum group metal elements such as palladium, rhodium, and iridium, and gold. For example, where the linearity of the relationship of electrical resistance variation to temperature change in the resistor wiring section 3 is regarded as a matter of importance, the greater the platinum content the better.

The metal material predominantly composed of platinum has a platinum content of about 80% by mass or above. Platinum and other element may either coexist in alloy form or exist in the form of mutually independent crystalline particles. Other material than the metallic component such as platinum or the metal material predominantly composed of platinum may be added to the resistor wiring section 3. Examples of such an additive material include particles of an inorganic substance similar to that contained in the insulating substrate 1, such as aluminum oxide. For example, the additive material is used to achieve a match in the degree of firing shrinkage between the resistor wiring section 3 and the insulating layer 1a.

To form the resistor wiring section 3, for example, a metallic paste prepared by kneading platinum powder in admixture with an organic solvent and a binder is applied, in a predetermined pattern, to the principal face, etc. of the ceramic green sheet which constitutes the insulating layer 1a, and, the applied paste and the ceramic green sheet are co-fired.

For example, with use of an external electric circuit, measurement is made of electrical resistance across the resistor wiring section 3, viz., between one end (first end A) and the opposite end (second end B) via first and second ends A' and B' of the individual layers and connection conductors 5 (through conductors) for providing connection among the resistor wiring section 3 layers as will hereafter be described. This electrical resistance varies according to the temperature of the resistor wiring section 3, and, the temperature of the resistor wiring section 3 varies according to the temperature of an environment where the sensor substrate 7, etc. is located (external temperature). That is, the detection of electrical resistance across the first end A and the second end B of the resistor wiring section 3 permits detection of external temperature.

Examples of the external temperature include the temperature of combustion exhaust gas of various types. In certain circumstances, a high temperature in the order of about several hundred degrees to a thousand degrees Celsius has to be detected. Thus, the resistor wiring section 3 is formed of platinum or a metal material predominantly composed of platinum to ensure stability even under such a high-temperature condition, and attain satisfactory linearity of the relationship of electrical resistance variation to a change in temperature. For example, the sensor substrate 7 provided with the electrode 2 is mounted on (connected to) an external substrate (not shown) comprising an electric circuit for resistance detection as described above (external electric circuit) to produce a sensor apparatus, and, such a sensor apparatus is installed in a location where an object under temperature measurement is placed (for example, gas flow channel).

When left exposed to outside air, the resistor wiring section 3 may undergo electrical resistance variation unnecessarily due to adhesion of foreign matter or damage caused by collision with the external substrate or other component mounted on the external substrate, for example. To prevent the unnecessary resistance variation, the resistor wiring section 3 is disposed in an inter-layer region, viz., interposed between the plurality of insulating layers 1a. In other words, the resistor wiring section 3 is disposed within the insulating substrate 1 to avoid exposure to the outside environment.

For example, the metallic layer 4 is formed of a metal material similar to that used for the resistor wiring section 3

(such as platinum) in a like manner. For example, the metallic layer 4 is formed of a metal material similar to that used for the resistor wiring section 3 (such as platinum) in a like manner. In this embodiment, the metallic layer 4 of the sensor substrate 7 is formed in a widened rectangular pattern from platinum. The electrode 2 may be configured differently, and, for example, it may be shaped in a strip having a bend.

Moreover, the electrode 2 disposed on the sensor substrate 7 serves to connect the resistor wiring section 3 to an external substrate comprising an external electric circuit. For example, the electrode 2 is formed of a metal material similar to that used for the resistor wiring section 3 (such as platinum) in a like manner. In this embodiment, the electrode 2 of the sensor substrate 7 is formed in a rectangular pattern from platinum. The electrode 2 may be configured differently, and, for example, it may be constructed of a gold-made lead terminal, not shown. Moreover, a lead terminal may be connected to the electrode 2 by means of resistance welding or otherwise.

As will hereafter be described, there may be a case where the electrode 2 is, together with the sensor substrate 7, placed in a high-temperature environment. It is thus preferable that the electrode 2 is formed of a metal material which is highly resistant to oxidation under high-temperature conditions, such as any of platinum group metal elements, including platinum, or gold.

The sensor substrate 7 thus constructed is provided with a temperature-sensing electrode 2 which is electrically connected to the resistor wiring section 3 of the sensor substrate 7. In this embodiment, electrical connection among the electrode 2, the resistor wiring section 3, and the metallic layer 4, as well as electrical connection among the resistor wiring section 3 layers, is established by a connection conductor (so-called via conductor) 5 provided so as to pass through the insulating layers 1a in a thickness direction.

For example, the connection conductor 5 is formed of a conductor material (metal material) predominantly composed of a metal material similar to that used for the resistor wiring section 3 (such as platinum). Examples of such a metal material include platinum, and a material predominantly composed of platinum with an inorganic filler, e.g. alumina filler added. For example, the inorganic filler serves for a match in the degree of shrinkage, shrinkage behavior, etc. between the connection conductor 5 and the insulating substrate 1 under a co-firing process.

For example, the connection conductor 5 is formed by applying a platinum paste similar to that used for forming the resistor wiring section 3 so as to fill a through hole formed in the ceramic green sheet which becomes the insulating layer 1a, and thereafter co-firing the paste and the ceramic green sheet. For example, the through hole is formed in the ceramic green sheet by mechanical punching operation using a metallic pin, or laser beam drilling, etc. In this case, inorganic filler particles as described above may be added to the metallic paste.

As shown in FIGS. 1 to 7, the sensor substrate 7 comprises: the insulating substrate 1; the electrode 2 disposed on the principal face of the insulating substrate 1; the resistor wiring section 3 in the form of multiple layers located within the insulating substrate 1, the layers being arranged in a thickness direction; and the widened metallic layer 4 disposed so as to overlap the electrode 2 as seen in the transparent plan view. With this construction, for example, in detecting combustion exhaust gas of various types, even if metal ions (positive ions) such as calcium ions contained in glass constituting the insulating substrate 1 are caused to migrate (diffuse) toward the electrode 2 (cathode) of the sensor substrate 7, the widened metallic layer 4, which overlaps the electrode 2 as seen in the transparent plan view, restrains the metal ions against migration toward the electrode 2. This makes it possible to protect the insulating substrate 1 from development of voids, etc., and render the resistor wiring section 3 less deformable for a reduction in the formation of a part subjected to a change in cross-sectional area, and thereby suppress the variation of resistance in the resistor wiring section 3.

Figure 2:
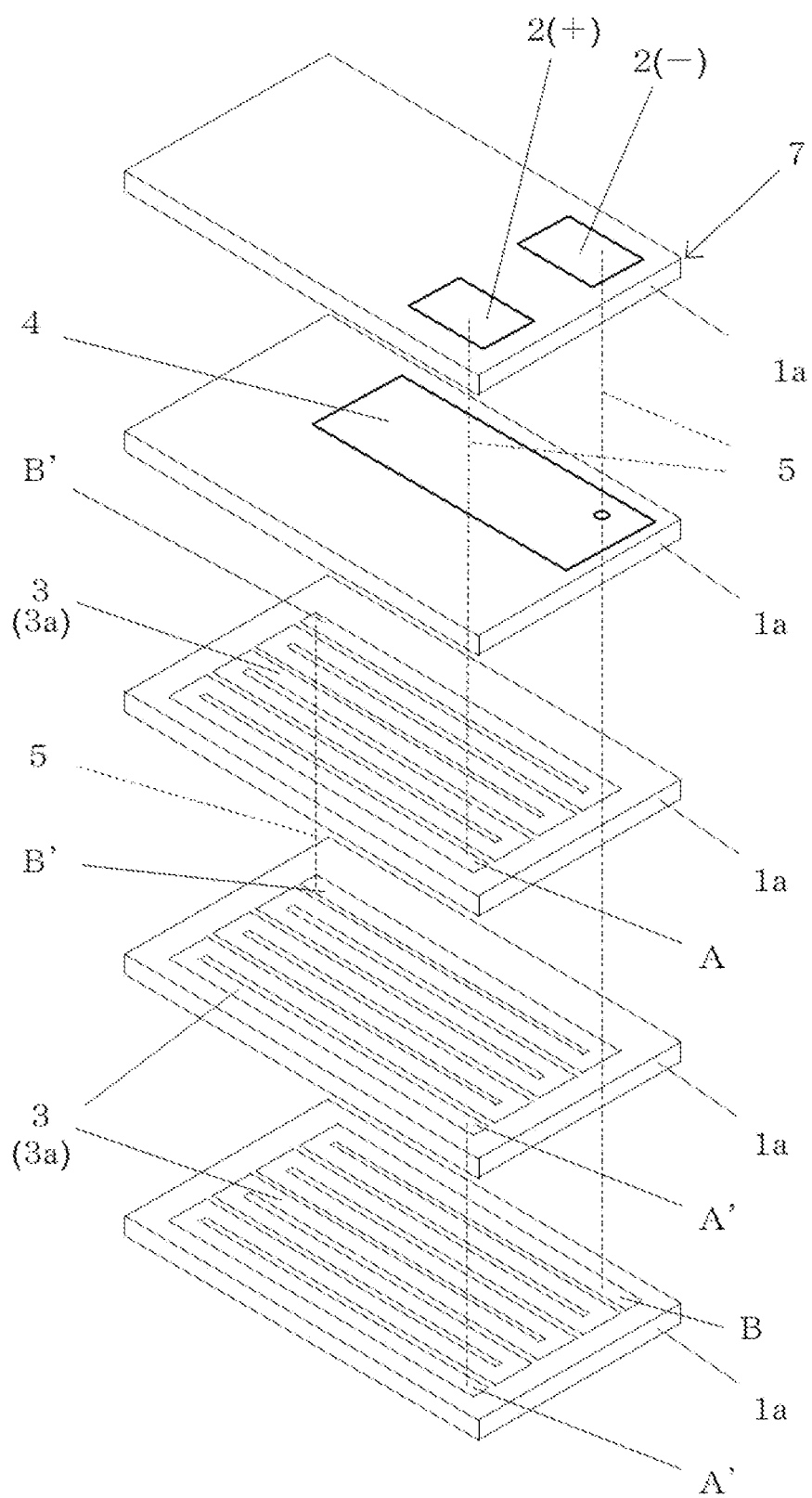
FIG. 2 is an exploded perspective view of the sensor substrate shown in FIG. 1.
Figure 3:
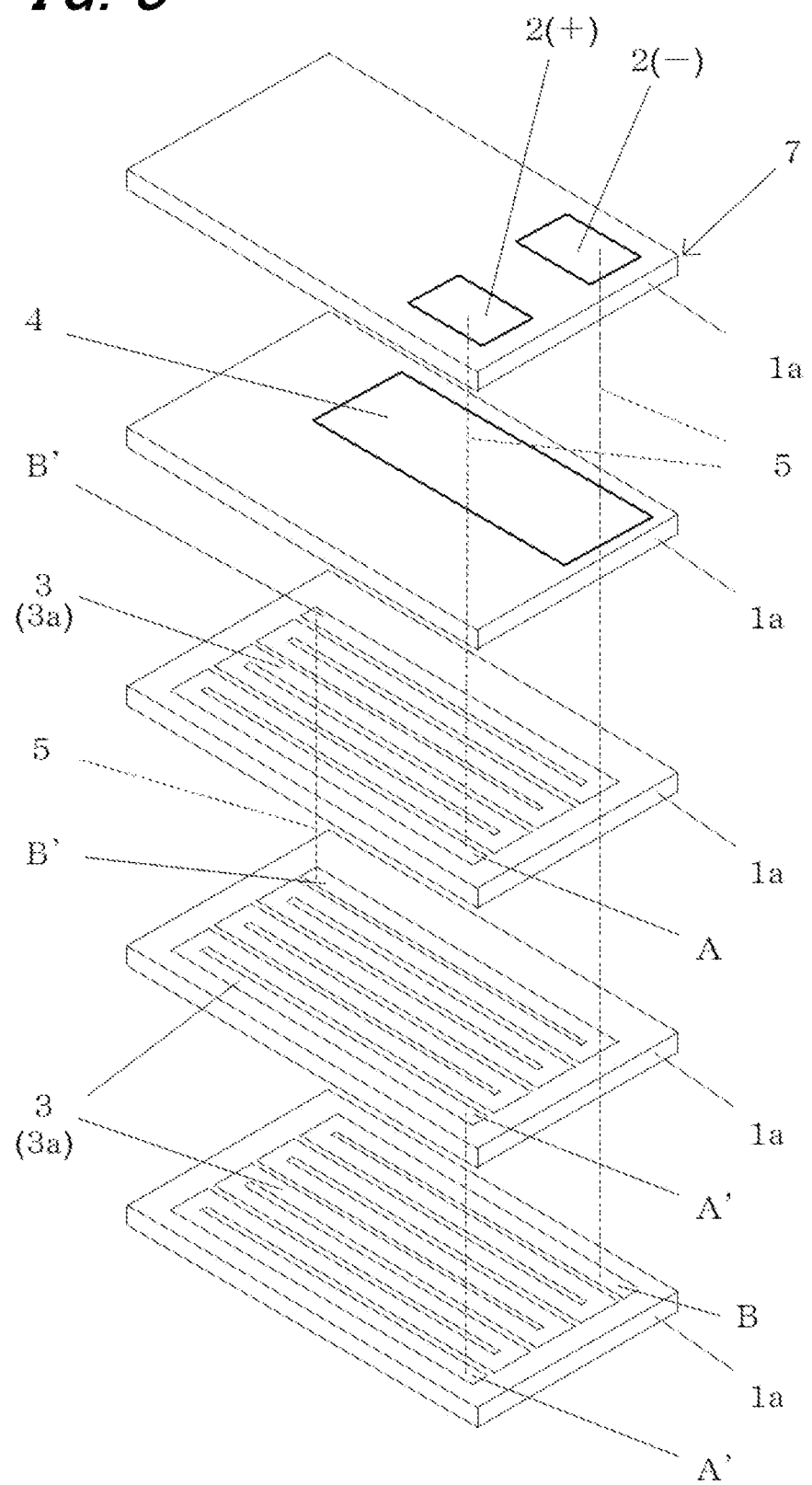
FIG. 3 is an exploded perspective view showing another modified example in the sensor substrate shown in FIG. 1, etc.
Figure 4:
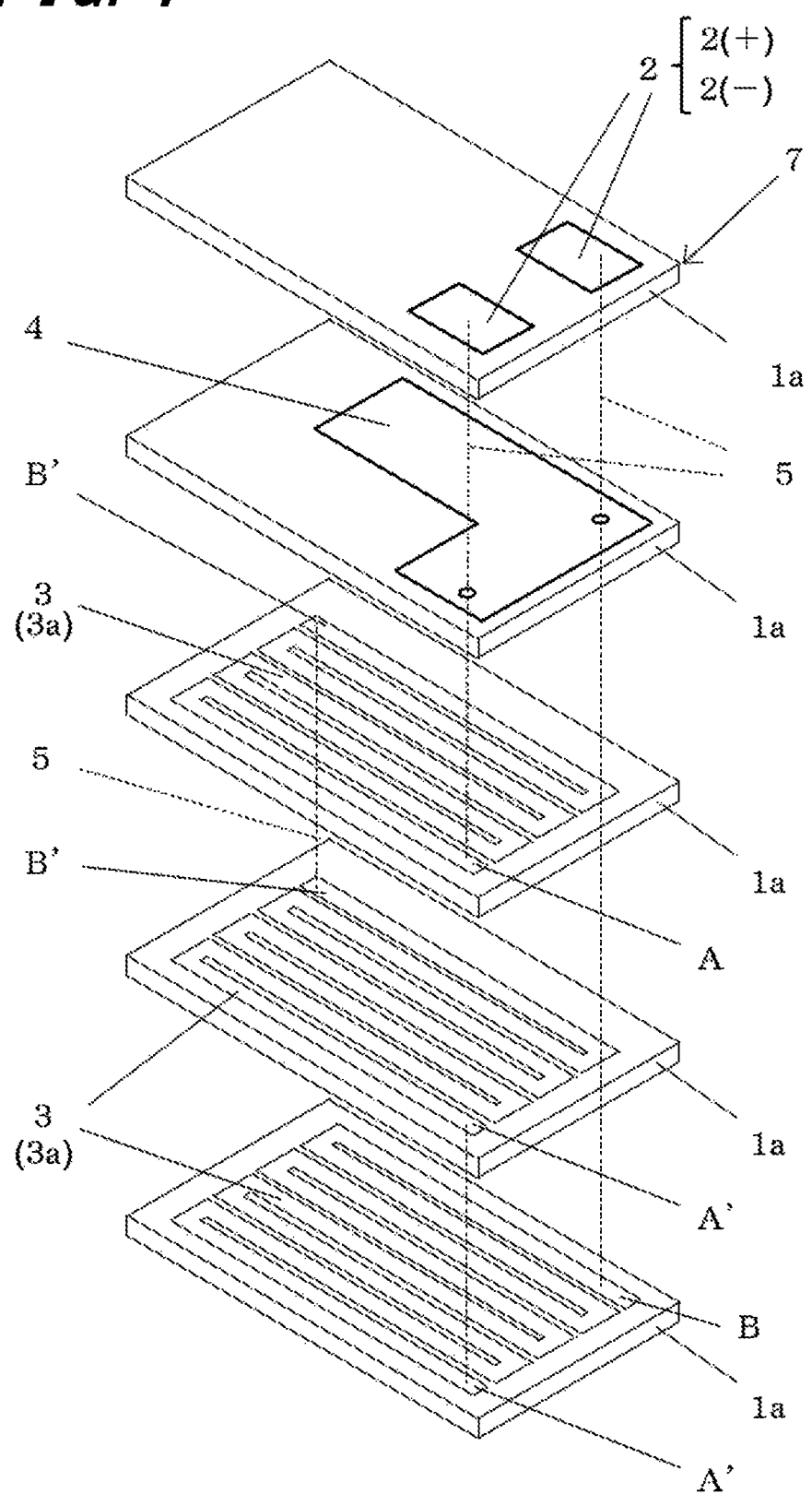
FIG. 4 is an exploded perspective view showing another modified example in the sensor substrate shown in FIG. 1, etc.
Figure 5:
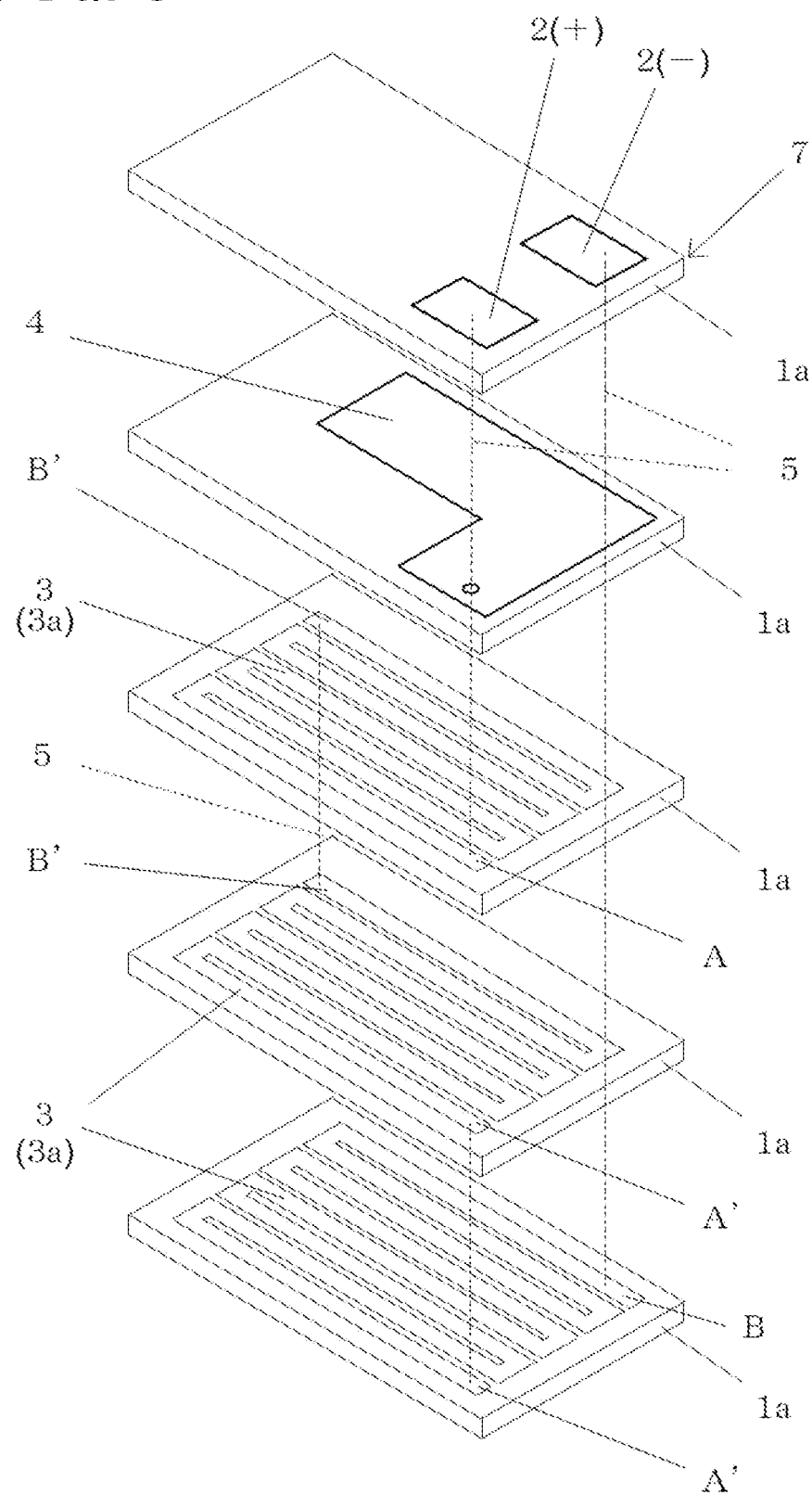
FIG. 5 is an exploded perspective view showing another modified example in the sensor substrate shown in FIG. 1, etc.
Figure 6:
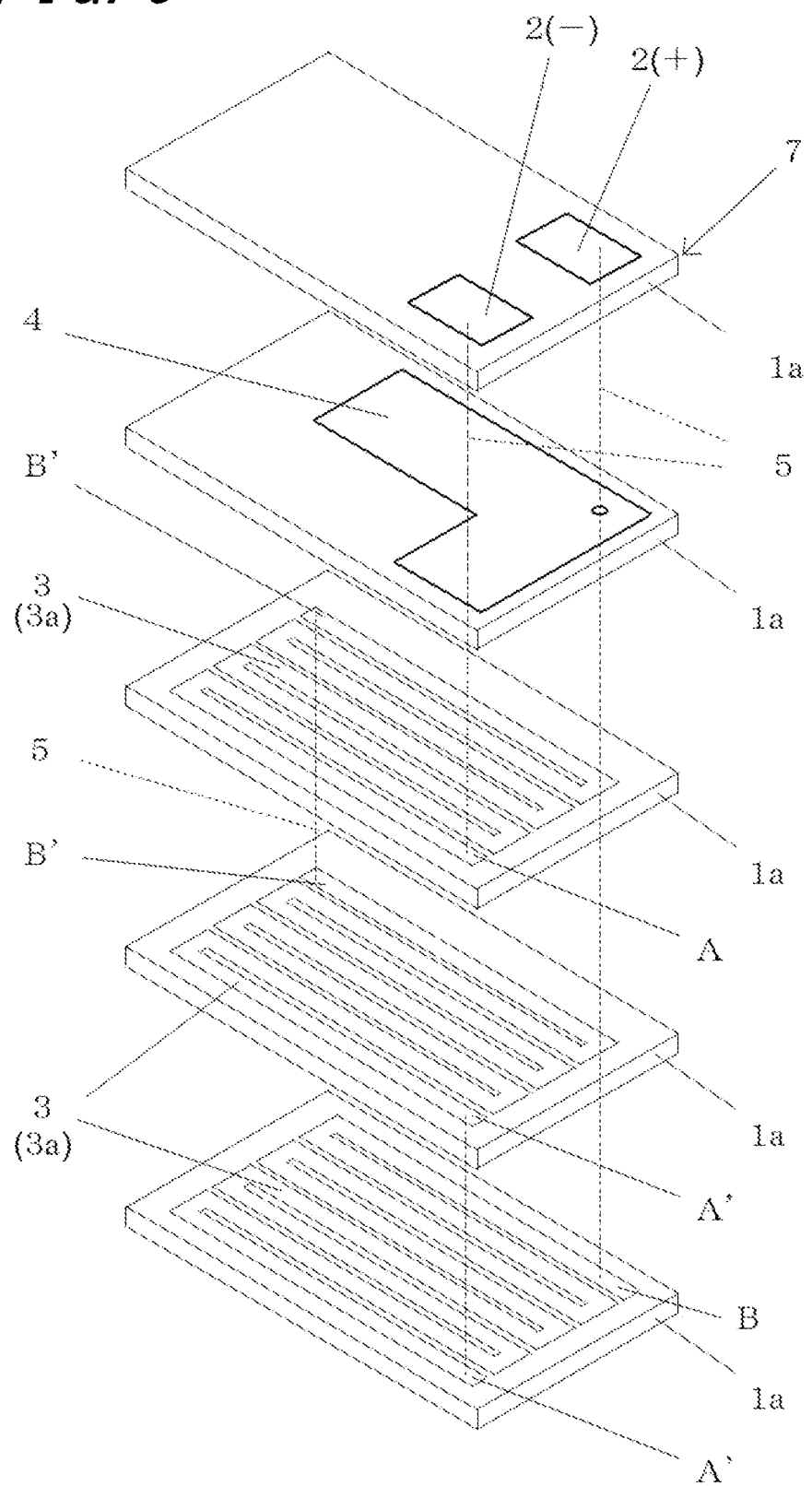
FIG. 6 is an exploded perspective view showing another modified example in the sensor substrate shown in FIG. 1, etc.

As the examples shown in FIGS. 1, 2, and 4, for example, where the metallic layer 4 has a hole, etc. formed therethrough and makes connection with neither the electrode 2 nor the resistor wiring section 3, under the consequent electrical independence of the metallic layer 4, even if metal ions contained in the insulating substrate 1 are caused to migrate (diffuse) toward the electrode 2 (anode and cathode) of the sensor substrate 7, the metallic layer 4 restrains the metal ions against migration toward the electrode 2. This makes it possible to protect the insulating substrate 1 from development of voids, etc., and render the resistor wiring section 3 less deformable for a reduction in the formation of a part subjected to a change in cross-sectional area, and thereby suppress the variation of resistance in the resistor wiring section 3.

Although the metallic layer 4 has a hole, etc. formed therethrough and makes connection with neither the electrode 2 nor the resistor wiring section 3 in the examples shown in FIGS. 1, 2, and 4, as shown in FIGS. 3 and 5 to 7, with the connection conductor 5 provided in the insulating substrate 1, the metallic layer 4 may be connected to the electrode 2 (cathode) and the resistor wiring section 3 via the connection conductor 5. With this arrangement, electrical connection is established between the electrode 2 (cathode) and the metallic layer 4, and thus, even if metal ions (positive ions) such as calcium ions contained in glass constituting the insulating substrate 1 are caused to migrate (diffuse) toward the electrode 2 (cathode) of the sensor substrate 7, the metallic layer 4 blocks migration of the metal ions toward the electrode 2 more reliably. This makes it possible to protect the insulating substrate 1 from development of voids, etc., and render the resistor wiring section 3 less deformable for a reduction in the formation of a part subjected to a change in cross-sectional area, and thereby suppress the variation of resistance in the resistor wiring section 3.

Moreover, as shown in FIG. 4, a through hole may be formed in the metallic layer 4 to prevent connection of the metallic layer 4 with the electrode 2 (anode) and the electrode 2 (cathode) via the connection conductor 5. This structure is desirable in that, for example, in detecting combustion exhaust gas of various types, even if the electrode 2 (anode) and the electrode 2 (cathode) are arranged in the place of each other, the detection of combustion exhaust gas of various types can be achieved.

Moreover, as shown in FIGS. 2 to 7, where the resistor wiring section 3 comprises a linear conductor 3a having a meandering configuration, and the metallic layer 4 overlaps the linear conductor 3a as seen in the transparent plan view, even if metal ions (positive ions) such as calcium ions contained in glass constituting a part of the insulating substrate 1 overlapping the linear conductor 3a are caused to migrate (diffuse) toward the electrode 2 (cathode) of the sensor substrate 7, the metallic layer 4 restrains the metal ions against migration toward the electrode 2 effectively. This makes it possible to protect the insulating substrate 1 from development of voids, etc., and render the resistor wiring section 3 less deformable for a reduction in the formation of a part subjected to a change in cross-sectional area, and thereby suppress the variation of resistance in the resistor wiring section 3 effectively.

Moreover, as shown in FIGS. 2 to 6, where the metallic layer 4 is located between the electrode 2 and the linear conductor 3*a* in the thickness direction of the insulating substrate 1, even if metal ions (positive ions) such as calcium ions contained in glass constituting the insulating substrate 1 are caused to migrate (diffuse) toward the electrode 2 (cathode) of the sensor substrate 7, the metallic layer 4, which is located between the electrode 2 and the linear conductor 3*a* in the thickness direction of the insulating substrate 1, restrains the metal ions against migration toward the electrode 2 more reliably. This makes it possible to protect the insulating substrate 1 from development of voids, etc., and render the resistor wiring section 3 less deformable for a reduction in the formation of a part subjected to a change in cross-sectional area, and thereby suppress the variation of resistance in the resistor wiring section 3.

Moreover, as shown in FIG. 1, where an auxiliary wiring 6*a* is mounted in a supplementary space 6 provided in the principal face (top surface) of the insulating substrate 1 so as to make connection with the resistor wiring section 3, expressed differently, where the principal face (top surface) of the insulating substrate 1 is provided with the auxiliary wiring 6*a* connected to the resistor wiring section 3, and also the metallic layer 4 is disposed so as not to overlap the auxiliary wiring 6*a*, as seen in the transparent plan view, then it is possible to adjust the resistance of the resistor wiring section 3 simply by cutting the auxiliary wiring 6*a*, while providing the above-described advantageous effects.

Figure 7:
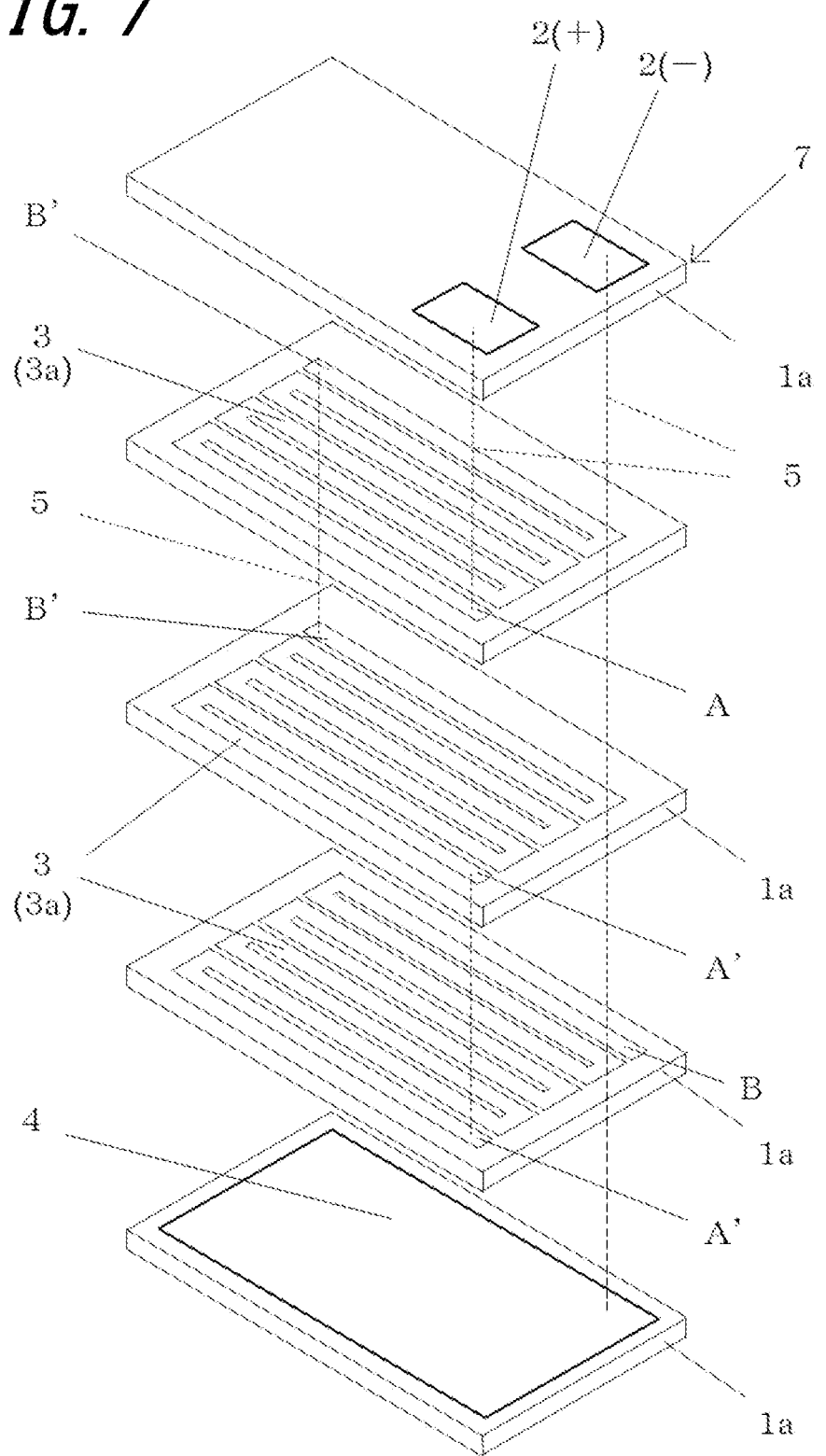
FIG. 7 is an exploded perspective view showing another modified example in the sensor substrate shown in FIG. 1, etc.

Moreover, as shown in FIG. 7, the insulating substrate 1 has another principal face (bottom surface), viz., the other principal face opposed to the principal face corresponding to the top surface, and, the metallic layer 4 is located between the other principal face and the linear conductor 3*a* in the thickness direction of the insulating substrate 1. In this example, the electrode 2 (cathode) and the metallic layer 4 are electrically connected to each other, and, the metallic layer 4 is located between the other principal face and the resistor wiring section 3 in the form of multiple layers. In this construction, even if metal ions (positive ions) such as calcium ions contained in glass constituting the insulating substrate 1 are caused to migrate (diffuse) toward the electrode 2 (cathode) of the sensor substrate 7, the metallic layer 4, which is opposed to the electrode 2 in the thickness direction of the insulating substrate 1, restrains the metal ions against migration toward the electrode 2 more effectively. This makes it possible to protect the insulating substrate 1 from development of voids, etc., and render the resistor wiring section 3 less deformable for a reduction in the formation of a part subjected to a change in cross-sectional area, and thereby suppress the variation of resistance in the resistor wiring section 3 more effectively. In this case, where the metallic layer 4 is made in planar configuration so as to cover the resistor wiring section 3 (the linear conductor 3*a*) as seen in the transparent plan view, migration of the metal ions toward the electrode 2 can be restrained by the metallic layer 4 more effectively.

Moreover, where the metallic layer 4 is wider at a region overlapping the linear conductor 3*a* than at a region overlapping the electrode 2, as seen in the transparent plan view, even if metal ions (positive ions) such as calcium ions contained in glass constituting the insulating substrate 1 are caused to migrate (diffuse) toward the electrode 2 (cathode) of the sensor substrate 7, the metallic layer 4, which is wider at the region overlapping the linear conductor 3*a* than at the other part, restrains the metal ions against migration toward the electrode 2 over a wide range. This makes it possible to protect the insulating substrate 1 from development of voids, etc., and render the resistor wiring section 3 less deformable for a reduction in the formation of a part subjected to a change in cross-sectional area, and thereby suppress the variation of resistance in the resistor wiring section 3 over a wide range.

Moreover, as shown in FIGS. 4 to 7, where a region of the metallic layer 4 encompasses a region of the electrode 2 as seen in the transparent plan view, the electrode 2 (anode) and the electrode 2 (cathode) are surrounded by the outer periphery of the metallic layer 4 as seen in the transparent plan view. In this arrangement, even if metal ions (positive ions) such as calcium ions contained in glass constituting a part of the insulating substrate 1 overlapping the linear conductor 3*a* are caused to migrate (diffuse) toward the electrode 2 (cathode) of the sensor substrate 7, the metallic layer 4 restrains the metal ions against migration toward the electrode 2 more effectively. This makes it possible to protect the insulating substrate 1 from development of voids, etc., and render the resistor wiring section 3 less deformable for a reduction in the formation of a part subjected to a change in cross-sectional area, and thereby suppress the variation of resistance in the resistor wiring section 3 more effectively.

According to the above-mentioned sensor substrate 7, the detection accuracy of temperature variation can be increased.

For example, for a measuring instrument that measures the temperature of exhaust gas from a combustor-equipped system such as an internal-combustion engine (gasoline engine, diesel engine, etc.), a gas turbine, or a boiler, with use of the above-described sensor substrate 7, temperature detection is effected in the following way. First, a sensor apparatus is prepared by installing the sensor substrate 7 in an external substrate comprising an electrical resistance detection circuit as described earlier connecting the electrode 2 of the sensor substrate 7 electrically to a predetermined location of the circuit of the external substrate. To establish the electrical connection, the electrode 2 and the circuit are connected to each other via solder, or a lead terminal (not shown) is connected to the electrode 2 by means of resistance welding or otherwise. Next, the sensor substrate 7 mounted in the sensor apparatus is installed within an exhaust gas channel. At this time, it is required that at least the sensor substrate 7 is located for exposure to exhaust gas, and thus other portions of the external substrate do not necessarily have to be located for exposure to exhaust gas. Then, the electrical resistance of the sensor substrate 7, as well as the electrical resistance across the first end A and the second end B of the resistor wiring section 3 included in the sensor substrate 7 varies according to the temperature of exhaust gas, and, the resulting electrical resistance value is measured by the electrical resistance detection circuit. On the basis of the measured electrical resistance, the temperature of the resistor wiring section 3, or equivalently the temperature of a place where the sensor substrate 7 bearing the resistor wiring section 3 is located can be detected with reference to the previously determined electrical resistance-temperature relationship, for example.

As described above, since the sensor apparatus is provided with the sensor substrate 7, the detection accuracy of temperature variation can be increased.

The line width of the resistor wiring section 3 is suitably determined according to various conditions including the measurement accuracy of a temperature to be detected, the range of to-be-detected temperatures, the thickness and length of the resistor wiring section 3, the distance from the outer edge of the insulating layer 1a to the resistor wiring section 3, and also productivity, economic efficiency, etc.

For example, under conditions where to-be-detected temperatures fall in a high-temperature range of about 500° C. to 1000° C., the resistor wiring section 3 is formed of platinum (such as so-called pure platinum having a platinum content of greater than or equal to 99.99% by mass), and the resistor wiring section 3 has a thickness of about 5 µm to 15 µm, then the line width of the resistor wiring section 3 is set at about 20 to 200 µm, for example.

In consideration of the setting of thickness, etc. of the resistor wiring section 3, it is preferable that the insulating layer 1a is formed of a ceramic sintered body, and the resistor wiring section 3 has the form of a thick-film conductor. In this case, for example, the resistor wiring section 3 is formed through a co-firing process with the insulating substrate 1 (the plurality of insulating layers 1a). If the resistor wiring section 3 composed of a thick-film conductor, a thickness thereof is easy to be set to a relatively large thickness as described above, such as about 10 µm or more. Moreover, since such a relatively thick resistor wiring section 3 is formed through a co-firing process with the insulating substrate 1, this is advantageous in terms of the strength of connection between the resistor wiring section 3 and the insulating substrate 1 and in terms of the productivity of the sensor substrate 7. In addition, the pattern of the resistor wiring section 3 can be determined easily by making adjustment to the pattern of the printed metallic paste which constitutes the resistor wiring section 3. This is also advantageous in terms of design flexibility, productivity, etc.

Moreover, as described above, the resistor wiring section 3 is designed in meandering configuration comprising a plurality of linear portions (no reference numeral) arranged in parallel with each other, and a plurality of folded portions (no reference numeral) which connect ends of linear portions arranged adjacent to each other out of the plurality of linear portions. The folded portions are staggered to connect respective alternate ends of a plurality of adjacent linear portions. In other words, the plurality of linear portions and the plurality of folded portions are sequentially connected in series to form a single meandering pattern (serpentine pattern).

In the case where the resistor wiring section 3 has the meandering pattern, since a relatively long resistor wiring section 3 is sequentially folded, such an arrangement of the resistor wiring section 3 is advantageous in providing as long a resistor wiring section 3 as possible in a single inter-layer region. Since the length of the resistor wiring section 3 is longer, electrical resistance between the first end A and the second end B of the resistor wiring section 3 can be further increased. That is, since the electrical resistance of the resistor wiring section 3 at a reference temperature (room temperature, for example) is relatively high, the absolute value of variation of electrical resistance according to temperature becomes larger. Therefore, accurate temperature measurement becomes easy from the room temperature to a high temperature range such as about 1000° C. mentioned above.

Moreover, for example, as the examples shown in FIGS. 1 to 7 in which the insulating layer 1a is quadrangular-shaped, where the resistor wiring section 3 is designed in a meandering configuration, the following effect can be obtained by arranging the linear portion and the folded portion of the resistor wiring section 3 of meandering configuration in parallel with the corresponding outer edges of the insulating layer 1a. That is, in this case, the linear portion of the resistor wiring section 3 nearest the outer edge of the insulating layer 1a and each folded portion of the resistor wiring section 3 are substantially equidistant from the corresponding outer edges of the insulating layer 1a. This helps reduce the likelihood that the resistor wiring section 3 is, at each of the linear portion and the folded portion, partly too close to the outer edge of the insulating layer 1a, causing platinum constituting the resistor wiring section 3 to sublime out.

Moreover, in this case, a relatively wide area of the linear portion and a relatively wide area of the folded portion may have substantially the same line width, and the distance between the linear portion and the corresponding outer edge of the insulating layer 1a and the distance between the folded portion and the corresponding outer edge of the insulating layer 1a may be substantially equal. This makes it possible to obtain a substantially uniform resistor wiring section 3-to-outer edge distance throughout the outer periphery of the insulating layer 1a, and thereby reduce the likelihood that platinum is urged to sublime out in a certain location in the length direction of the resistor wiring section 3.

Thus, where the temperature measurement accuracy and long-term reliability are regarded as a matter of importance, in the sensor substrate 7, it is preferable that the resistor wiring section 3 has a meandering configuration in which the linear portion and the folded portion are arranged in parallel with the corresponding outer edges of the insulating layer 1a. Moreover, where the insulating layer 1a (insulating substrate 1) is quadrangular-shaped, for example, in manufacturing the sensor substrates 7 in the form of a segmentable substrate in which a plurality of regions each constituting the insulating substrate are arranged and formed on a single base substrate, an arrangement of the plurality of regions is easy. That is, it is more advantageous in productivity, economic efficiency, etc. of the sensor substrates 7.

Moreover, in the examples shown in FIGS. 1 to 7, the insulating substrate 1 is shaped in a quadrangular (rectangular) plate, and, in the resistor wiring section 3 having a meandering pattern, each linear portion is placed along the long side of the rectangular insulating layer 1a (inter-later region). Moreover, each folded portion is placed along the short side of the insulating layer 1a. In this case, for example, when applying the metallic paste for forming the resistor wiring section 3 by means of screen printing or otherwise, the following advantageous effect can be obtained. That is, in the printing process, the spread of the metallic paste tends to occur at a folded section (a boundary between the folded portion and the linear portion). Thus, a reduction in the number of the folded portions helps reduce the spread of the metallic paste, and increase the resistance value of the resistor wiring section 3 as a whole accordingly. In this embodiment, since this folding is less than in a case where the length of the linear portion is short and the number of the folded portions is large, it is easier to increase the total resistance value.

It should be understood that the sensor substrate 7 of the invention is not limited to the embodiments as described herein above, and that various changes and modifications are possible without departing from the scope of the invention. For example, the resistor wiring section 3 may be disposed in each of four or more inter-layer regions. Moreover, the resistor wiring section 3 of the sensor substrate 7 is not limited to a meandering conductor, but may be of a conductor having a different pattern.

The invention claimed is:

1. A sensor substrate, comprising:
an insulating substrate;
an electrode disposed on a principal face of the insulating substrate;
a resistor wiring section in a form of multiple layers located within the insulating substrate, wherein the multiple layers are disposed in a thickness direction of the insulating substrate and the resistor wiring section comprises a linear conductor having a meandering configuration;
an auxiliary wiring disposed on the principal face so as to be connected to the resistor wiring section; and
a widened metallic layer disposed so as to overlap the electrode and not to overlap the auxiliary wiring, as seen in a transparent plan view of the sensor substrate, wherein the widened metallic layer overlaps the linear conductor.

2. A sensor substrate, comprising:
an insulating substrate;
an electrode disposed on a principal face of the insulating substrate;
a resistor wiring section in a form of multiple layers located within the insulating substrate, wherein the multiple layers are disposed in a thickness direction of the insulating substrate and the resistor wiring section comprises a linear conductor having a meandering configuration; and
a widened metallic layer disposed so as to overlap the electrode and the linear conductor, as seen in a transparent plan view of the sensor substrate, wherein the widened metallic layer is located between the electrode and the linear conductor in the thickness direction of the insulating substrate.

3. A sensor substrate, comprising:
an insulating substrate, wherein the insulating substrate has a second principal face opposed to a first principal face;
an electrode disposed on the first principal face of the insulating substrate;
a resistor wiring section in a form of multiple layers located within the insulating substrate, wherein the multiple layer are disposed in a thickness direction of the insulating substrate and the resistor wiring section comprises a linear conductor having a meandering configuration; and
a widened metallic layer disposed so as to overlap the electrode and the linear conductor, as seen in a transparent plan view of the sensor substrate, wherein the widened metallic layer is located between the second principal face and the linear conductor in the thickness direction of the insulating substrate.

4. The sensor substrate according to claim 1, further comprising:
a connection conductor disposed in the insulating substrate,
wherein the electrode, the resistor wiring section, and the widened metallic layer are connected to one another via the connection conductor.

5. The sensor substrate according to claim 1,
wherein the widened metallic layer is not connected to the electrode and the resistor wiring section.

6. A sensor apparatus, comprising:
the sensor substrate according to claim 1; and
an external substrate connected with the sensor substrate.

7. The sensor substrate according to claim 1,
wherein the widened metallic layer is wider at a region overlapping the linear conductor than at a region overlapping the electrode, as seen in the transparent plan view.

8. The sensor substrate according to claim 1,
wherein a region of the widened metallic layer encompasses a region of the electrode, as seen in the transparent plan view.

9. The sensor substrate according to claim 7,
wherein a region of the widened metallic layer encompasses a region of the electrode, as seen in the transparent plan view.

10. The sensor substrate according to claim 1,
wherein the widened metallic layer is located between the electrode and the linear conductor in the thickness direction of the insulating substrate.

11. The sensor substrate according to claim 7,
wherein the widened metallic layer is located between the electrode and the linear conductor in the thickness direction of the insulating substrate.

12. The sensor substrate according to claim 1,
wherein the insulating substrate has another principal face opposed to the principal face, and
the widened metallic layer is located between the another principal face and the linear conductor in the thickness direction of the insulating substrate.

13. The sensor substrate according to claim 7,
wherein the insulating substrate has another principal face opposed to the principal face, and
the widened metallic layer is located between the another principal face and the linear conductor in the thickness direction of the insulating substrate.

14. The sensor substrate according to claim 2, further comprising:
a connection conductor disposed in the insulating substrate,
wherein the electrode, the resistor wiring section, and the widened metallic layer are connected to one another via the connection conductor.

15. The sensor substrate according to claim 2,
wherein the widened metallic layer is not connected to the electrode and the resistor wiring section.

16. A sensor apparatus, comprising:
the sensor substrate according to claim 2; and
an external substrate connected with the sensor substrate.

17. The sensor substrate according to claim 3, further comprising:
a connection conductor disposed in the insulating substrate,
wherein the electrode, the resistor wiring section, and the widened metallic layer are connected to one another via the connection conductor.

18. The sensor substrate according to claim 3,
wherein the widened metallic layer is not connected to the electrode and the resistor wiring section.

19. A sensor apparatus, comprising:
the sensor substrate according to claim 3; and
an external substrate connected with the sensor substrate.

* * * * *